United States Patent
Nouwen et al.

(12)
(10) Patent No.: US 6,525,222 B2
(45) Date of Patent: Feb. 25, 2003

(54) PROCESS FOR PREPARING AMINES

(75) Inventors: Jan Nouwen, Lorsch; Arthur Höhn, Kirchheim; Horst Neuhauser, Dudenhofen; Frank Funke, Frankenthal; Stephan Andreas Schunk, Heidelberg; Johann-Peter Melder, Böhl-Iggelheim; Knut Eger, Limburgerhof; Michael Hesse, Worms; Joachim Wulff-Döring, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/729,458

(22) Filed: Dec. 5, 2000

(65) Prior Publication Data

US 2001/0003136 A1 Jun. 7, 2001

(30) Foreign Application Priority Data

Dec. 6, 1999 (DE) .......... 199 58 700

(51) Int. Cl.$^7$ .......... C07C 209/00
(52) U.S. Cl. .......... 564/472; 564/347; 564/397; 564/446; 564/480; 564/401; 564/447; 564/349; 564/479; 546/184; 546/246; 544/59; 544/106
(58) Field of Search .......... 564/397, 446, 564/480, 349, 347, 473, 401, 447, 472, 479; 546/184, 246; 544/106, 59

(56) References Cited

U.S. PATENT DOCUMENTS

| | | | | |
|---|---|---|---|---|
| 4,014,933 A | 3/1977 | Boettger et al. | ............ | 260/563 |
| 4,234,727 A | 11/1980 | Toussaint | .................... | 544/178 |
| 5,002,922 A | 3/1991 | Irgang | ........................ | 502/331 |
| 5,166,433 A | 11/1992 | Irgang et al. | ............... | 564/105 |
| 5,530,127 A | 6/1996 | Reif | ............................ | 544/106 |
| 5,608,113 A | 3/1997 | Becker | ........................ | 564/480 |
| 5,952,529 A | 9/1999 | Chang et al. | ............... | 564/480 |
| 6,057,442 A | 5/2000 | Wulff-Doering | ............ | 544/106 |

FOREIGN PATENT DOCUMENTS

| | | |
|---|---|---|
| DE | 1817691 | 6/1970 |
| DE | 1953263 | 2/1972 |
| DE | 1793220 | 3/1972 |
| DE | 1543354 | 4/1972 |
| DE | 2219475 | 11/1973 |
| DE | 28 38 184 | 3/1980 |
| DE | 198 59776 | 6/2000 |
| DE | 199 10960 | 9/2000 |
| EP | 284398 | 9/1988 |
| EP | 382 049 | 8/1990 |
| EP | 514 692 | 11/1992 |
| EP | 696 572 | 2/1996 |
| EP | 697 395 | 2/1996 |
| EP | 905 122 | 3/1999 |
| EP | 963 975 | 12/1999 |
| EP | 1035106 | 9/2000 |
| GB | 1190435 | 5/1970 |
| GB | 1218454 | 1/1971 |
| GB | 1421278 | 1/1976 |

OTHER PUBLICATIONS

Abst. 71:38326=DE 1803083; 1970.
Abst. 46450170=DE 1817691; 1970.
Abst. 74:76004=FR 1590871; 1970.
Abst. 39 095 170=DE 1803083; 1970.
Abst. 111:161414=HU 47456; 1989.
Derwent Abst. 97 385916=CN 11 10 629; 1995.
Abst. 76368/70=DL 75086, 1968.

Primary Examiner—Richard L. Raymond
Assistant Examiner—Kahsay Habte
(74) Attorney, Agent, or Firm—Keil & Weinkauf

(57) ABSTRACT

Amines are prepared by reacting aldehydes or ketones at elevated temperature under elevated pressure with nitrogen compounds selected from the group of ammonia, primary and secondary amines, and with hydrogen in the presence of a catalyst, wherein the catalytically active mass of the catalyst contains, after its preparation and before the treatment with hydrogen,

- 22 to 45% by weight of oxygen-containing compounds of zirconium, calculated as $ZrO_2$,
- 1 to 30% by weight of oxygen-containing compounds of copper, calculated as CuO,
- 5 to 50% by weight of oxygen-containing compounds of nickel, calculated as NiO, where the molar ratio of nickel to copper is greater than 1,
- 5 to 50% by weight of oxygen-containing compounds of cobalt, calculated as CoO,
- 0 to 5% by weight of oxygen-containing compounds of molybdenum, calculated as $MoO_3$, and 0 to 10% by weight of oxygen-containing compounds of aluminum and/or manganese, calculated as $Al_2O_3$ or $MnO_2$.

10 Claims, No Drawings

PROCESS FOR PREPARING AMINES

The present invention relates to a process for preparing amines by reacting aldehydes or ketones at elevated temperature under elevated pressure with nitrogen compounds selected from the group of ammonia, primary and secondary amines, and with hydrogen in the presence of a catalyst.

EP-A-514 692 discloses catalysts containing oxides of copper, nickel and/or cobalt, zirconium and/or aluminum for the catalytic amination of alcohols in the gas phase with ammonia or primary amines and hydrogen.

This patent application discloses that the atomic ratio of nickel to copper in these catalysts must be from 0.1 to 1.0, preferably 0.2 to 0.5 (page 2, lines 47 to 48; cf. also loc. cit.: Example 1) since, otherwise, yield-reducing byproducts are formed to an increased extent in the amination of alcohols (loc. cit.: Examples 6 and 12). Aluminum oxide is preferably used as support (loc. cit.: Examples 1 to 5 and 7 to 11).

EP-A-382 049 discloses catalysts containing oxygen-containing zirconium, copper, cobalt and nickel compounds, and processes for the hydrogenating amination of alcohols or carbonyl compounds. The preferred zirconium oxide content of these catalysts is 70 to 80% by weight (loc. cit.: page 2, last paragraph; page 3, 3rd paragraph; Examples). Although these catalysts have good activity and selectivity, their useful lives are in need of improvement.

EP-A-696 572 and EP-A-697 395 disclose catalysts containing oxides of nickel, copper, zirconium and molybdenum for the catalytic amination of alcohols with nitrogen compounds in the presence of hydrogen.

Earlier German application No. 19910950.5 of Mar. 12, 1999 discloses catalysts containing oxides of nickel, copper and zirconium for the catalytic amination of aldehydes or ketones with nitrogen compounds in the presence of hydrogen. The catalysts preferably contain no catalytically active amounts of cobalt. Although these catalysts have a good activity, their mechanical stabilities and selectivities require improvement.

EP-A-905 122 relates to a process for preparing amines by reacting primary or secondary alcohols with nitrogen compounds selected from the group of ammonia and primary and secondary amines at elevated temperatures and pressures with hydrogen in the presence of catalysts containing zirconium, copper and nickel but no cobalt.

The earlier European application No. 99111282.2 of Jun. 10, 1999, relates to a process for preparing amines by reacting primary or secondary alcohols with nitrogen compounds selected from the group of ammonia, primary and secondary amines, at elevated temperatures and pressures with hydrogen in the presence of catalysts containing zirconium, copper, nickel and cobalt.

Earlier German application No. 19859776.2 of Dec. 23, 1998 describes a process for preparing amines by reacting primary or secondary alcohols, aldehydes or ketones with nitrogen compounds at elevated temperatures and pressures in the presence of hydrogen and a catalyst containing copper and oxygen-containing titanium compounds, the catalyst being employed in the form of shaped articles produced with the addition of metallic copper powder.

DE-A-28 38 184 describes a process for preparing tertiary amines by reacting secondary amines with alcohols or carbonyl compounds under hydrogenating conditions in the gas phase, by undertaking the reaction on a copper catalyst which has been obtained by thermal decomposition and reduction of a basic copper aluminum carbonate.

Disadvantages of prior art processes are that the selectivities and yields achieved in the aminating hydrogenation of aldehydes and ketones are too low and/or the catalysts show inadequate activity and/or stability under the reaction conditions.

It is an object of the present invention to improve, by remedying the disadvantages of the prior art, the economics of the processes used to date for the hydrogenating amination of aldehydes and ketones. It was intended to find catalysts which can be prepared industrially in a simple manner and which permit the hydrogenating amination of aldehydes and ketones to be carried out with high conversion of aldehyde or ketone, in particular conversions of 90 to 100%, high yield, high selectivity, in particular selectivities of 95 to 100% (based on the aldehyde or ketone) and long catalyst life with, at the same time, high mechanical stability of the catalyst shaped article (e.g. measured as side crushing strength). The catalysts ought accordingly to have a high activity and a high chemical and mechanical stability under the reaction conditions.

We have found that this object is achieved by a process for preparing amines by reacting aldehydes or ketones at elevated temperature under elevated pressure with nitrogen compounds selected from the group of ammonia, primary and secondary amines, and with hydrogen in the presence of a catalyst, wherein the catalytically active mass of the catalyst contains, after its preparation and before the treatment with hydrogen, 22 to 45% by weight of oxygen-containing compounds of zirconium, calculated as $ZrO_2$, 1 to 30% by weight of oxygen-containing compounds of copper, calculated as $CuO$, 5 to 50% by weight of oxygen-containing compounds of nickel, calculated as $NiO$, where the molar ratio of nickel to copper is greater than 1, 5 to 50% by weight of oxygen-containing compounds of cobalt, calculated as $CoO$, 0 to 5% by weight of oxygen-containing compounds of molybdenum, calculated as $MoO_3$, and 0 to 10% by weight of oxygen-containing compounds of aluminum and/or manganese, calculated as $Al_2O_3$ or $MnO_2$.

The catalysts in the process according to the invention are generally employed preferably in the form of catalysts which consist only of catalytically active mass and, where appropriate, a molding auxiliary (such as graphite or stearic acid) if the catalyst is employed as shaped articles, that is to say contain no other catalytically inactive constituents.

The catalytically active mass can be introduced into the reaction vessel after grinding as powder or as chips or, preferably, introduced into the reactor after grinding, mixing with shaping auxiliaries, shaping and heat-treating, as catalyst shaped articles—for example as tablets, beads, rings, extrudates (e.g. ribbons).

The concentrations (in % by weight) stated for the components of the catalyst are in each case—unless stated otherwise—based on the catalytically active mass of the prepared catalyst after its last heat treatment and before the treatment with hydrogen.

The catalytically active mass of the catalyst after its last heat treatment and before the treatment with hydrogen is defined as the total of the masses of the catalytically active constituents and of the support materials and essentially comprises oxygen-containing compounds of zirconium, oxygen-containing compounds of copper, oxygen-containing compounds of nickel, oxygen-containing compounds of cobalt and, optionally, oxygen-containing compounds of molybdenum and/or oxygen-containing compounds of aluminum and/or oxygen-containing compounds of manganese.

The total of the abovementioned catalytically active constituents and of the abovementioned support materials in the catalytically active mass, calculated as $ZrO_2$, CuO, NiO, CoO, $MoO_3$, $Al_2O_3$ and $MnO_2$, is normally from 70 to 100% by weight, preferably 80 to 100% by weight, particularly preferably 90 to 100% by weight, in particular 95 to 100% by weight, very particularly 100% by weight.

The catalytically active mass of the catalysts employed in the process according to the invention may furthermore comprise one or more elements (oxidation state 0) or their inorganic or organic compounds selected from groups I A to VI A and I B to VII B and VIII of the periodic table.

Examples of such elements or compounds thereof are:

transition metals such as Re or rhenium oxides, Cr or chromium oxides, W or tungsten oxides, Ta or tantalum oxides, Nb or niobium oxides or niobium oxalate, V or vanadium oxides or vanadyl pyrophosphate, lanthanides such as Ce or $CeO_2$, or Pr or $Pr_2O_3$, alkali metal oxides such as $Na_2O$, alkali metal carbonates such as $Na_2CO_3$ and $K_2CO_3$, alkaline earth metal oxides such as SrO, alkaline earth metal carbonates such as $MgCO_3$, $CaCO_3$ and $BaCO_3$, boron oxide ($B_2O_3$).

The catalytically active mass of the catalysts employed in the process according to the invention contains, after its preparation and before the treatment with hydrogen, 22 to 45% by weight, preferably 22 to 39% by weight, particularly preferably 25 to 39% by weight, of oxygen-containing compounds of zirconium, calculated as $ZrO_2$, 1 to 30% by weight, preferably 2 to 25% by weight, particularly preferably 5 to 15% by weight, of oxygen-containing compounds of copper, calculated as CuO, 5 to 50% by weight, preferably 15 to 45% by weight, particularly preferably 21 to 40% by weight, of oxygen-containing compounds of nickel, calculated as NiO, where the molar ratio of nickel to copper is greater than 1, preferably greater than 1.2, particularly preferably 1.5 to 8.5, 5 to 50% by weight, preferably 20 to 45% by weight, particularly preferably 21 to 40% by weight, of oxygen-containing compounds of cobalt, calculated as CoO, 0 to 5% by weight, particularly preferably 0.1 to 0.5% by weight, of oxygen-containing compounds of molybdenum, calculated as $MoO_3$, and 0 to 10% by weight of oxygen-containing compounds of aluminum and/or manganese, calculated as $Al_2O_3$ or $MnO_2$, where the ratio by weight of oxygen-containing compounds of zirconium, calculated as $ZrO_2$, to the oxygen-containing compounds of aluminum and/or manganese, calculated as $Al_2O_3$ or $MnO_2$, is preferably at least 2.5, particularly preferably at least 5, very particularly preferably 0% by weight of oxygen-containing compounds of aluminum and/ or manganese.

The catalysts preferably employed in the process according to the invention have a catalytically active mass after their preparation and before the treatment with hydrogen which contains 5 to 15% by weight of oxygen-containing compounds of copper, calculated as CuO, and in total 35 to 69% by weight of oxygen-containing compounds of nickel, calculated as NiO, and oxygen-containing compounds of cobalt, calculated as CoO, where the content of oxygen-containing compounds of cobalt, calculated as CoO, based on the total of oxygen-containing compounds of nickel, calculated as NiO, and oxygen-containing compounds of cobalt, calculated as CoO, is at least 1.7% by weight, in particular at least 12.0% by weight, very particularly preferably at least 40% by weight.

Various procedures are possible for preparing the catalysts. They can be obtained, for example, by peptization of powdered mixtures of the hydroxides, carbonates, oxides and/or other salts of the components with water and subsequent extrusion and heat treatment of the mass obtained in this way.

However, precipitation methods are generally used to prepare the catalysts according to the invention. Thus, they can be obtained for example by a joint precipitation of the nickel, cobalt and copper components from an aqueous salt solution containing these elements by use of mineral bases in the presence of a suspension of an oxygen-containing zirconium compound of low solubility, and subsequent washing, drying and calcining of the resulting precipitate. Examples of oxygen-containing zirconium compounds of low solubility which can be used are zirconium dioxide, zirconium oxide hydrate, zirconium phosphates, borates and silicates. The suspensions of the zirconium compounds of low solubility can be prepared by suspending fine-particle powders of these compounds in water with vigorous stirring. These suspensions are advantageously obtained by precipitating the zirconium compounds of low solubility from aqueous zirconium salt solutions with use of mineral bases.

The catalysts according to the invention are prepared in particular by a joint precipitation (coprecipitation) of all their components. This is expediently done by adding an aqueous mineral base, in particular an alkali metal base, for example sodium carbonate, sodium hydroxide, potassium carbonate or potassium hydroxide, to an aqueous salt solution containing the catalyst components at elevated temperature and with stirring until the precipitation is complete. The nature of the salts used is generally not critical: since what mainly matters with this procedure is the solubility of the salts in water, one criterion is that they have a good solubility in water necessary to prepare these relatively highly concentrated salt solutions. It is regarded as self-evident that, when selecting the salts of the individual components, the salts chosen are, of course, only those with anions which do not interfere, whether by causing unwanted precipitations or by impeding or preventing the precipitation by complex formation.

The precipitates obtained in these precipitation reactions are generally not chemically homogeneous and consist, inter alia, of mixtures of the oxides, oxide hydrates, hydroxides, carbonates and insoluble and basic salts of the metals employed. It may prove to be beneficial for the filterability of the precipitates if they are aged, i.e. if they are left alone for some time after the precipitation, where appropriate at elevated temperature or while passing air through.

The precipitates obtained after these precipitation processes are further processed to the catalysts according to the invention in a conventional way. After washing, they are dried, generally at 80 to 200° C., preferably at 100 to 150° C., and then calcined. The calcination (heat treatment) is generally carried out at temperatures between 300 and 800° C., preferably at 400 to 600° C., in particular at 450 to 550° C.

After the calcination, the catalyst is expediently conditioned, whether by grinding it to a particular particle size or admixed, after its grinding, with molding aids such as graphite or stearic acid, compressing to shaped articles by means of a tablet press, and heat treating. The temperatures of the heat treatment generally correspond to the temperatures for the calcination.

The catalysts prepared in this way contain the catalytically active metals in the form of a mixture of their oxygen-containing compounds, i.e. in particular as oxides and mixed oxides.

The prepared catalysts can be stored as such. Before being used as catalysts for the hydrogenating amination of aldehydes or ketones, they are normally reduced by treatment with hydrogen. However, they can also be employed without this prior reduction, in which case they are reduced by the hydrogen present in the reactor under the conditions of the hydrogenating amination. For the prior reduction, the catalysts are generally first exposed to a nitrogen/hydrogen atmosphere at 150 to 200° C. over a period of 12 to 20 hours, and then treated in a hydrogen atmosphere at 200 to 400° C. for up to about 24 hours. In this prior reduction, some of the oxygen-containing metal compounds present in the catalysts are reduced to the corresponding metals, so that these are present, together with the various types of oxygen compounds, in the active form of the catalyst.

A particular advantage of the catalysts employed in the process according to the invention is their mechanical stability, i.e. their hardness. The mechanical stability can be determined by measuring the side crushing strength. To do this, the catalyst shaped article, e.g. the catalyst tablet, is exposed to an increasing force between two parallel plates, e.g. on the convex surface of the catalyst tablets, until the catalyst shaped article fractures. The force recorded when the catalyst shaped article fractures is the side crushing strength.

Amines of the general formula I

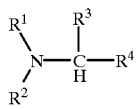

(I)

in which $R^1$, $R^2$ are hydrogen, $C_{1-20}$-alkyl, $C_{3-12}$-cycloalkyl, aryl, $C_{7-20}$-aralkyl and $C_{7-20}$-alkylaryl or together are $(CH_2)_j$—X—$(CH_2)_k$, $R^3$, $R^4$ are hydrogen, alkyl such as $C_{1-200}$-alkyl, cycloalkyl such as $C_{3-12}$-cycloalkyl, hydroxyalkyl such as $C_{1-20}$-hydroxyalkyl, aminoalkyl such as $C_{1-20}$-aminoalkyl, hydroxyalkylaminoalkyl such as $C_{1-20}$-hydroxyalkylaminoalkyl, alkoxyalkyl such as $C_{2-30}$-alkoxyalkyl, dialkylaminoalkyl such as $C_{3-30}$-dialkylaminoalkyl, alkylaminoalkyl such as $C_{2-30}$-alkylaminoalkyl, $R^5$-$(OCR^6R^7CR^8R^9)_n$—$(OCR^6R^7)$, aryl, hetaryl, aralkyl such as $C_{7-20}$-aralkyl, hetarylalkyl such as $C_{4-20}$-hetarylalkyl, alkylaryl such as $C_{7-20}$-alkylaryl, alkylhetaryl such as $C_{4-20}$-alkylhetaryl and Y—$(CH_2)_m$—$NR^5$—$(CH_2)_q$ or together are $(CH_2)_l$—X—$(CH_2)_m$ or $R^2$ and $R^4$ are together $(CH_2)_l$—X—$(CH_2)_m$, $R^5R^{10}$ are hydrogen, $C_{1-4}$-alkyl, $C_{7-40}$-alkylphenyl, $R^6$, $R^7$, $R^8$, $R^9$ are hydrogen, methyl or ethyl, is $CH_2$, $CHR^5$, oxygen (O), sulfur (S) or $NR^5$, is $N(R^{10})_2$, hydroxyl, $C_{2-20}$-alkylaminoalkyl or $C_{3-20}$-dialkylaminoalkyl, n is an integer from 1 to 30 and j, k, l, m, q are an integer from 1 to 4 are of particular commercial interest.

The process according to the invention is therefore preferably used to prepare amines I by reacting aldehydes or ketones of the formula II or III

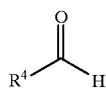

(II)

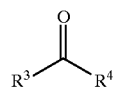

(III)

with nitrogen compounds of the general formula IV

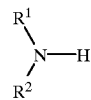

(IV)

where $R^1$, $R^2$, $R^3$ and $R^4$ have the abovementioned meanings.

As is evident from the definitions for the radicals $R^2$ and $R^4$, an intramolecular reaction in an appropriate amino ketone or amino aldehyde is also possible.

The substituents $R^1$, $R^2$, $R^3$, $R^4$, $R^5$, $R^6$, $R^7$, $R^8$, $R^9$, $R^{10}$, the variables X, Y and the indices j, k, l, m, n and q in the compounds I, II, III and IV have, independently of one another, the following meanings:

$R^1$, $R^2$, $R^3$, $R^4$, $R^5$, $R^6$, $R^7$, $R^8$, $R^9$, $R^{10}$
  hydrogen (H), $R^3$, $R^4$ $C_{1-200}$-alkyl, preferably $C_{1-14}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, particularly preferably isopropyl, 2-ethylhexyl, n-decyl, 2-n-propyl-n-heptyl, n-tridecyl, 2-n-butyl-n-nonyl and 3-n-butyl-n-nonyl, and preferably $C_{40-200}$-alkyl such as polybutyl, polyisobutyl, polypropyl, polyisopropyl and polyethyl, particularly preferably polybutyl and polyisobutyl, $C_{1-20}$-hydroxyalkyl, preferably $C_{1-8}$-hydroxyalkyl, particularly preferably $C_{1-4}$-hydroxyalkyl, such as hydroxymethyl, 1-hydroxyethyl, 2-hydroxyethyl, 1-hydroxy-n-propyl, 2-hydroxy-n-propyl, 3-hydroxy-n-propyl and 1-hydroxymethylethyl, $C_{1-20}$-aminoalkyl, preferably $C_{1-8}$-aminoalkyl such as aminomethyl, 2-aminoethyl, 2-amino-1,1-dimethylethyl, 2-amino-n-propyl, 3-amino-n-propyl, 4-amino-n-butyl, 5-amino-n-pentyl, N-(aminoethyl)aminoethyl and N-(aminoethyl)aminomethyl, $C_{1-20}$-hydroxyalkylaminoalkyl, preferably $C_{1-8}$-hydroxyalkylaminoalkyl such as (2-hydroxyethylamino)methyl, 2-(2-hydroxyethylamino)ethyl and 3-(2-hydroxyethylamino)propyl, $C_{2-30}$-alkoxyalkyl, preferably $C_{2-20}$-alkoxyalkyl, particularly preferably $C_{2-8}$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_2$- to $C_4$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, $R^5$-$(OCR^6R^7CR^8R^9)_n$—$(OCR^6R^7)$, preferably $R^5$-$(OCHR^7CHR^9)_n$—$(OCR^6R^7)$, particularly preferably $R^5$-$(OCH_2CHR^9)_n$—$(OCR^6R^7)$, $C_{3-30}$-dialkylaminoalkyl, preferably $C_{3-20}$-dialkylaminoalkyl, particularly preferably $C_{3-10}$-N,N-dialkylaminoalkyl such as N,N-dimethylaminomethyl, 2-(N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino)ethyl and 2-(N,N-diisopropylamino)ethyl, $(R^5)_2N$—$(CH_2)_q$, $C_{2-30}$-alkylaminoalkyl, preferably $C_{2-20}$-alkylaminoalkyl, particularly preferably $C_{2-8}$-alkylaminoalkyl such as methylaminomethyl, methylaminoethyl, ethylaminomethyl, ethylaminoethyl and isopropylaminoethyl, $(R^5)HN$—$(CH_2)_q$, Y—$(CH_2)_m$—$NR^5$—$(CH_2)_q$, $C_{4-20}$-hetarylalkyl such as 2-pyridylmethyl, 2-furanylmethyl, 3-pyrrolylmethyl and 2-imidazolylmethyl, $C_{4-20}$-alkylhetaryl such as 2-methyl-3-pyridinyl, 4,5-dimethyl-2-imidazolyl, 3-methyl-2-furanyl and 5-methyl-2-pyrazinyl, hetaryl such as 2-pyridinyl, 3-pyridinyl, 4-pyridinyl, pyrazinyl, 3-pyrrolyl, 2-imidazolyl, 2-furanyl and 3-furanyl, $R^1$, $R^2$, $R^3$, $R^4$ $C_{3-12}$-cycloalkyl, preferably $C_{3-8}$-cycloalkyl such as cyclopropyl, cyclobutyl, cyclopentyl, cyclohexyl, cycloheptyl and cyclooctyl, particularly preferably cyclopentyl, cyclohexyl and cyclooctyl, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, $C_{7-20}$-alkylaryl, preferably $C_{7-12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, $C_{7-20}$-aralkyl, preferably $C_{7-12}$-phenylalkyl such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $R^3$ and $R^4$ or $R^2$ and $R^4$ together a —$(CH_2)_l$—X—$(CH_2)_m$— group, such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)_2$—O—$(CH_2)_2$—, —$(CH_2)_2$—$NR^5$—$(CH_2)_2$—, —$CH_2$—O—$(CH_2)_3$—, —$CH_2$—$NR^5$—$(CH_2)_3$—, $R^1$, $R^2$ $C_{1-20}$-alkyl, preferably $C_{1-8}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_{1-4}$-alkyl such as methyl, ethyl, n-propyl, isopropyl, n-butyl, isobutyl, sec-butyl and tert-butyl, $R^1$ and $R^2$ together a —$(CH_2)_j$—X—$(CH_2)_k$— group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)_2$—O—$(CH_2)_2$—, —$(CH_2)_2$—$NR^5$—$(CH_2)_2$—, —$CH_2$—O—$(CH_2)_3$—, —$CH_2$—$NR^5$—$(CH_2)_3$—, $R^5$, $R^{10}$ $C_{1-4}$-alkyl, such as methyl, ethyl, n-propyl, isopropyl, n-butyl, isobutyl, sec-butyl and tert-butyl, preferably methyl and ethyl, particularly preferably methyl, $C_{7-40}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, $R^6$, $R^7$, $R^8$, $R^9$ methyl and ethyl, preferably methyl,

X $CH_2$, $CHR^5$, oxygen (O), sulfur (S) or $NR^5$, preferably $CH_2$ and O,

Y $N(R^{10})_2$, preferably $NH_2$ and $N(CH_3)_2$, hydroxyl, $C_{2-20}$-alkylaminoalkyl, preferably $C_{2-16}$-alkylaminoalkyl, such as methylaminomethyl, methylaminoethyl, ethylaminomethyl, ethylaminoethyl and isopropylaminoethyl, $C_{3-20}$-dialkylaminoalkyl, preferably $C_{3-16}$-dialkylaminoalkyl such as dimethylaminomethyl, dimethylaminoethyl, diethylaminoethyl, di-n-propylaminoethyl and diisopropylaminoethyl, j, l an integer from 1 to 4 such as 1, 2, 3 and 4, preferably 2 and 3, particularly preferably 2, k, m, q an integer from 1 to 4 such as 1, 2, 3 and 4, preferably 2, 3 and 4, particularly preferably 2 and 3, n an integer from 1 to 10, preferably an integer from 1 to 8 such as 1, 2, 3, 4, 5, 6, 7 or 8, particularly preferably an integer from 1 to 6 such as 1, 2, 3, 4, 5 or 6.

Ketones which are suitable for use in the process according to the invention are virtually all aliphatic and aromatic ketones. The aliphatic ketones may be straight-chain, branched or cyclic, and the ketones may contain heteroatoms. To date no restrictions are known on the number of carbons in the ketones which can be aminated. The ketones may moreover have substituents which are inert under the conditions of the hydrogenating amination, for example alkoxy, alkenyloxy, alkylamino or dialkylamino groups. If it is intended to aminate polyfunctional ketones, it is possible by controlling the reaction conditions to obtain amino ketones, amino alcohols, cyclic amines or polyaminated products.

Examples of ketones which preferably undergo the aminating hydrogenation are the following:

acetone, ethyl methyl ketone, methyl vinyl ketone, isobutyl methyl ketone, 3-methyl-2-butanone, diethyl ketone, tetralone, acetophenone, p-methylacetophenone, p-methoxyacetophenone, n-methoxyacetophenone, 1-acetylnaphthalene, 2-acetylnaphthalene, 1-phenyl-3-butanone, cyclobutanone, cyclopentanone, cyclopentenone, cyclohexanone, cyclohexenone, 2,6-dimethylcyclohexanone, cycloheptanone, cyclododecanone, acetylacetone, methylglyoxal and benzophenone.

Aldehydes suitable for use in the process according to the invention are virtually all aliphatic and aromatic aldehydes. The aliphatic aldehydes may be straight-chain, branched or cyclic, and the aldehydes may contain heteroatoms. To date no restrictions are known on the number of carbons in the aldehydes which can be aminated. The aldehydes may moreover have substituents which are inert under the conditions of the hydrogenating amination, for example alkoxy, alkenyloxy, alkylamino or dialkylamino groups. If it is intended to aminate polyfunctional aldehydes or keto aldehydes, it is possible by controlling the reaction conditions to obtain amino alcohols, cyclic amines or polyaminated products.

Examples of aldehydes which preferably undergo the aminating hydrogenation are the following:
formaldehyde, acetaldehyde, propionaldehyde, n-butyraldehyde, isobutyraldehyde, pivalaldehyde, n-pentanal, n-hexanal, 2-ethylhexanal, 2-methylpentanal, 3-methylpentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, 4-formyltetrahydropyran, 3-formyltetrahydrofuran, 5-formylvaleronitrile, citronellal, acrolein, methacrolein, ethylacrolein, citral, crotonaldehyde, 3-methoxypropionaldehyde, 3-aminopropionaldehyde, hyderoxypivalaldehyde, dimethylolpropionaldehyde, dimethylolbutyraldehyde, furfural, glyoxal, glutaraldehyde and hydroformylated oligomers and polymers such as hydroformylated polyisobutene (polyisobutenealdehyde) or oligomer obtained by metathesis with 1-pentene and cyclopentene and hydroformylated.

The aminating agents which can be employed in the hydrogenating amination of aldehydes and ketones are both ammonia and primary or secondary, aliphatic, cycloaliphatic or aromatic amines.

For use of ammonia as aminating agent, the carbonyl groups are initially converted into free amino groups ($-NH_2$). The primary amines formed in this way can react with hydroxyl or further carbonyl groups to give the corresponding secondary amines, and these in turn can react with hydroxyl or further carbonyl groups to give the corresponding, where appropriate symmetrical, tertiary amines. It is possible in this way to prepare as required preferentially primary, secondary or tertiary amines, depending on the composition of the reaction mixture and on the reaction conditions used—pressure, temperature, reaction time, molar ratios.

It is possible in this way to prepare cyclic amines such as pyrrolidines, piperidines, hexamethyleneimines, piperazines and morpholines from aldehydes or ketones having more than one aldehyde or keto group or from keto aldehydes by intramolecular hydrogenating amination.

Primary or secondary amines can be used as aminating agents just like ammonia.

These aminating agents are preferably used to prepare asymmetrically substituted di- or trialkylamines such as ethyldiisopropylamine and ethyldicyclohexylamine. Examples of mono- and dialkylamines which are preferably used as aminating agents are the following: methylamine, dimethylamine, ethylamine, diethylamine, propylamine, diisopropylamine, butylamine, pentylamine, hexylamine and cyclohexylamine.

The aminating agent can be employed in stoichiometric amount relative to the carbonyl group which is to undergo aminating hydrogenation. However, an excess of aminating agent is preferably used, generally a more than 1.05 molar excess per mole of carbonyl group which is to undergo aminating hydrogenation. Ammonia in particular is generally employed in a 1.05 to 250-fold, preferably 2 to 100-fold, in particular 2 to 50-fold, molar excess per mole of carbonyl group to be reacted. Larger excesses of ammonia and of primary or secondary amines are possible.

The process according to the invention can be carried out batchwise or, preferably, continuously as follows, with the catalyst preferably being arranged as fixed bed in the reactor.

Amination of the aldehyde groups or keto groups in the precursor can be carried out in the liquid phase or in the gas phase.

The reaction is normally carried out at temperatures from 50 to 250° C., preferably 50 to 200° C., in particular 60 to 170° C.

The reaction is generally carried out under a pressure of 1 to 400 bar (0.1 to 40 MPa). Pressures of 10 to 250 bar, in particular of 20 to 200 bar, are preferably used.

It is possible to use higher temperatures and a higher total pressure. The total pressure in the reaction vessel, which derives from the total of the partial pressures of the aminating agent, of the carbonyl component, of the reaction products and of the solvent which is also used where appropriate, at the stated temperatures, is expediently adjusted by injecting hydrogen to the pressure required for the reaction.

The amount of hydrogen generally fed into the reaction is 5 to 400 1(STP), preferably 50 to 200 1(STP), per mole of carbonyl component, the liter data having been in each case converted to standard conditions (STP).

The reaction generally takes place without additional solvent. When reacting high molecular weight starting compounds which have high viscosity or are solid at room temperature or when reacting to give corresponding products, it may be advantageous also to use a solvent which is inert under the reactions conditions, such as methanol, ethanol, propanol, tetrahydrofuran, dioxane, N-methylpyrrolidone, Mihagol or ethylene glycol dimethyl ether.

It may be advantageous for the selectivity of the present process to mix the catalyst shaped articles in the reactor with inert packings in order as it were to dilute them. The proportion of the packings in such catalyst preparations can be 20 to 80, especially 30 to 60 and, in particular, 40 to 50 parts by volume.

The procedure in practice is generally to feed the aldehyde or the ketone and the aminating agents simultaneously into the catalyst, which is normally present in a fixed bed reactor, preferably heated from outside, and which is at the required reaction temperature and the required pressure. The space velocity in this case is generally from 0.01 to 5, preferably 0.05 to 3, particularly preferably 0.1 to 1.6, 1 of aldehyde or ketone per liter of catalyst and hour. It is expedient in this connection to heat the reactants before feeding into the reaction vessel.

The reactants can be passed either upwards or else downwards through the reactor. It is self-evident that the process can be carried out either batchwise or continuously. In both cases, the excess aminating agent can be recycled together with the hydrogen. If the conversion in the reaction is not complete, the unreacted starting material can likewise be fed back into the reaction zone.

After expediently decompressing the discharge from the reactor, the excess aminating agent and the hydrogen are removed, and the resulting aminated products are purified by distillation, liquid extraction or crystallization. The excess aminating agent and hydrogen are advantageously fed back into the reaction zones. The same applies to any unreacted or incompletely reacted carbonyl component or a corresponding alcohol component produced by hydrogenation.

The water formed during the reaction generally has no adverse effect on the degree of conversion, the reaction rate, the selectivity and the catalyst life and is therefore expediently removed from the reaction product only when it is worked up by distillation.

The amines obtainable by the process according to the invention are suitable inter alia as intermediates in the preparation of fuel additives (U.S. Pat. No. 3,275,554; DE-A-21 25 039 and DE-A-36 11 230), surfactants, drugs and crop protection agents, and of vulcanization accelerators.

EXAMPLES

A) Preparation of catalyst A (according to the invention)

An aqueous solution of nickel nitrate, copper nitrate, cobalt nitrate and zirconium acetate containing 2.39% by weight NiO, 2.39% by weight CoO, 0.94% by weight CuO and 2.82% by weight $ZrO_2$ was precipitated with a 20% strength by weight aqueous sodium carbonate solution simultaneously at a constant flow rate in a stirred vessel at a temperature of 70° C. in such a way that the pH of 7.0 measured with a glass electrode was maintained.

The resulting suspension was filtered, and the filter cake was washed with deionized water until the electrical conductivity of the filtrate was about 20 mS. The filter cake was then dried at a temperature of 150° C. in a drying oven or a spray dryer. The hydroxide/carbonate mixture obtained in this way was then heat-treated at a temperature of 500° C. for a period of 4 hours.

The catalyst A obtained in this way had the composition: 28% by weight NiO, 28% by weighs CoO, 11% by weight CuO and 33% by weight $ZrO_2$.

The catalyst powder was mixed with 3% by weight graphite and shaped to 5×3 mm tablets.

B) Preparation of catalyst B (according to EP-A-382 049, page 6; for comparative test)

An aqueous solution of zirconium, copper(II), cobalt(II) and nickel(II) salts was pumped simultaneously with aqueous sodium carbonate solution with a density of 1.208 kg/l into a precipitation apparatus which contained freshly precipitated zirconium dioxide suspended in water. The pH of the solution was kept content at 6.0 during the precipitation and, after the metal salt solution was consumed, raised to pH 7.5 by adding aqueous sodium carbonate solution. The precipitate was washed, dried to constant weight at 120° C. and calcined to constant weight at 400° C. The resulting catalyst mass was ground, mixed with 3% by weight of graphite, tabletted and again calcined at 520° C. for 3 hours.

The catalyst B obtained in this way had the composition: 76% by weight $ZrO_2$, 4% by weight CuO, 10% by weight CoO and 10% by weight NiO.

C) Mechanical stability of the catalysts according to the invention

The mechanical stability of catalysts with 11% by weight CuO, 33% by weight $ZrO_2$ and a total of 56% by weight [NiO+CoO] with various NiO/CoO ratios, prepared as described for catalyst A), was measured.

This was done by treating the catalysts under reaction conditions for 16 hours as follows (=boiling test) and then testing their mechanical properties by measuring their side crushing strength.

This entailed charging an autoclave with 30 g of catalyst (in a basket), 67 ml of isopropylamine, 67 ml of acetone and 16 ml of water. The autoclave was closed and then flushed with argon. The contents of the autoclave were stirred at 700 revolutions/min during the reaction time. 50 bar of $H_2$ were then injected and the contents of the reactor were brought to 130° C. within 120 minutes. The pressure was increased with $H_2$ to 200 bar and stirred at the particular temperature for 16 h. Cooling the autoclave was followed by very slow decompression in order to avoid disintegration of the catalyst shaped article through the expansion of gaseous reactants in the shaped article during the decompression.

After removal of the tablets their hardness was checked by measuring the side crushing strength.

| CoO content of the catalyst in % by weight, where [NiO + CoO] = 56% by weight | CoO content based on the [NiO + CoO] total content in % by weight | Side crushing strength (in N) after carrying out the boiling test |
|---|---|---|
| 0 | 0.0 | 4 |
| 5 | 8.9 | 9 |
| 12 | 21.4 | 13 |
| 28 | 50.0 | 27 |

The side crushing strength of the catalyst shaped articles increases with increasing CoO/NiO ratio.

The catalysts preferred for the process according to the invention have, after the above-defined boiling test, a side crushing strength of at least 5 newton, in particular of at least 10 newton, very especially of at least 20 newton.

The side crushing strength was determined as follows:

The catalyst tablet was exposed to an increasing force on the convex surface between two parallel plates until fracture occurred. The force recorded at fracture is the side crushing strength. The determination was carried out in a tester supplied by Zwick, Ulm, with stationary rotating plate and freely moveable vertical plunger which pressed the shaped article against the stationary rotating plate. The freely moveable plunger was connected to a pressure cell for recording the force. The apparatus was controlled by a computer which recorded and analyzed the measurements. 25 satisfactory (i.e. without cracks and without chipped edges) tablets were taken from a thoroughly mixed sample of the catalyst and the side crushing strength of each of them was measured and then averaged.

Example 1
Continuous amination of cyclopentanone

A continuously operated high-pressure reactor was packed with 500 $cm^3$ of catalyst A and charged hourly from the base with 300 $cm^3$ of cyclopentanone and 750 g of liquid ammonia. The catalyst temperature was set at 150° C. and the pressure in the reactor was set at 200 bar by a simultaneous injection of hydrogen. The discharge from the reaction was decompressed and then excess ammonia was distilled off. The collected discharges from the reaction were analyzed by gas chromatography: cyclopentylamine was obtained in a yield of 98.1%.

Example 2
Batchwise amination of α-tetralone

A 300 ml autoclave with magnetic stirrer and catalyst basket was charged with 30 ml of α-tetralone and 30 ml of catalyst A. 70 ml of ammonia were then injected. While stirring, hydrogen was injected to 100 bar, the temperature was raised to 100° C. and hydrogen was injected to 200 bar. The autoclave was stirred at 100° C. for 12 h. The discharge from the reaction was measured by gas chromatography (Rtx-5-amine column). The amine 1,2,3,4-tetrahydro-1-naphthylamine was obtained in a yield of 97.9%.

Example 3
Continuous amination of p-methoxybenzaldehyde (anisaldehyde) to give p-methoxybenzylamine A continuously operated laboratory apparatus (direct transit, 100 ml catalyst volume) was packed with catalyst A. Ammonia was then injected cold (30 bar) and the reactor was heated to 130° C. A pressure of 200 bar was set with hydrogen.

a) 65.5 g/h anisaldehyde and 53 g/h ammonia were passed with 20 l (Stp)/h hydrogen at 130° C. upward over the catalyst: yield 98.6%.

b) 67.5 g/h anisaldehyde and 53 g/h ammonia were passed with 20 l (Stp)/h hydrogen at 120° C. upward over the catalyst: yield 99.2%.

c) 32.7 g/h anisaldehyde and 26 g/h ammonia were passed with 20 l (Stp)/h hydrogen at 130° C. upward over the catalyst: yield 98.5%.

Example 4 (Comparative Example)

Example No. 1 for the continuous amination of cyclopentanone was carried out as described with the difference that catalyst B was employed.

The catalyst had disintegrated after the test had lasted a few days (<10), and thus showed inadequate mechanical stability and was therefore unsuitable.

Example 5
Continuous amination of α-indanone

A continuously operated high-pressure reactor was packed with 250 cm$^3$ of catalyst A and, at 130° C. and 100 bar, charged hourly from the base with 32 g of a methanolic α-indanone solution (80% by weight indanone), 55 ml of liquid ammonia and 15 l (Stp) of hydrogen. Excess ammonia and methanol were then distilled off. The collected discharges from the reaction were analyzed by gas chromatography: 1-aminoindane was obtained in a yield of 91.8%.

We claim:

1. A process for preparing amines by reacting aldehydes or ketones at elevated temperature under elevated pressure with nitrogen compounds selected from the group of ammonia, primary and secondary amines, and with hydrogen in the presence of a catalyst, wherein the catalytically active mass of the catalyst contains, after its preparation and before the treatment with hydrogen, 22 to 45% by weight of oxygen-containing compounds of zirconium, calculated as $ZrO_2$, 1 to 30% by weight of oxygen-containing compounds of copper, calculated as CuO, 5 to 50% by weight of oxygen-containing compounds of nickel, calculated as NiO, where the molar ratio of nickel to copper is greater than 1, 5 to 50% by weight of oxygen-containing compounds of cobalt, calculated as CoO, 0 to 5% by weight of oxygen-containing compounds of molybdenum, calculated as $MoO_3$, and 0 to 10% by weight of oxygen-containing compounds of aluminum and/or manganese, calculated as $Al_2O_3$ or $MnO_2$.

2. A process as claimed in claim 1, wherein the catalytically active mass of the catalyst contains, after its preparation and before the treatment with hydrogen, 22 to 39% by weight of oxygen-containing compounds of zirconium, calculated as $ZrO_2$, 2 to 25% by weight of oxygen-containing compounds of copper, calculated as CuO, 15 to 45% by weight of oxygen-containing compounds of nickel, calculated as NiO, where the molar ratio of nickel to copper is greater than 1, 20 to 45% by weight of oxygen-containing compounds of cobalt, calculated as CoO, 0 to 5% by weight of oxygen-containing compounds of molybdenum, calculated as $MoO_3$, and 0 to 10% by weight of oxygen-containing compounds of aluminum and/or manganese, calculated as $Al_2O_3$ or $MnO_2$.

3. A process as claimed in claim 1, wherein the catalytically active mass of the catalyst contains, after its preparation and before the treatment with hydrogen, 25 to 39% by weight of oxygen-containing compounds of zirconium, calculated as $ZrO_2$.

4. A process as claimed in claim 1, wherein the catalytically active mass of the catalyst contains, after its preparation and before the treatment with hydrogen, 5 to 15% by weight of oxygen-containing compounds of copper, calculated as CuO.

5. A process as claimed in claim 1, wherein the catalytically active mass of the catalyst contains, after its preparation and before the treatment with hydrogen, in total 35 to 69% by weight of oxygen-containing compounds of nickel, calculated as NiO, and oxygen-containing compounds of cobalt, calculated as CoO, where the content of oxygen-containing compounds of cobalt, calculated as CoO, based on the total of oxygen-containing compounds of nickel, calculated as NiO, and oxygen-containing compounds of cobalt, calculated as CoO, is at least 12.0% by weight, in particular at least 40% by weight.

6. A process as claimed in claim 1, wherein the catalytically active mass of the catalyst contains, after its preparation and before the treatment with hydrogen, 0.1 to 5% by weight of oxygen-containing compounds of molybdenum, calculated as $MoO_3$.

7. A process as claimed in claim 1, wherein the reaction is carried out under pressures of from 0.1 to 40 MPa.

8. A process as claimed in claim 1, wherein the reaction is carried out at temperatures of from 50 to 250° C.

9. A process as claimed in claim 1, wherein the catalyst is employed in the form of shaped articles.

10. A process as claimed in claim 1 for preparing amines of the formula I

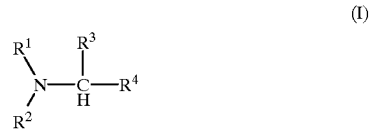

(I)

in which $R^1$, $R^2$ are hydrogen, $C_{1-20}$-alkyl, $C_{3-12}$-cycloalkyl, aryl, $C_{7-20}$-aralkyl and $C_{7-20}$-alkylaryl or together are $(CH_2)_j$—X—$(CH_2)_k$, $R^3$, $R^4$ are hydrogen, alkyl, cycloalkyl, hydroxyalkyl, aminoalkyl, alkanolaminoalkyl, alkoxyalkyl, dialkylaminoalkyl, alkylaminoalkyl, $R^5$-$(OCR^6R^7CR^8R^9)_n$—$(OCR^6R^7)$, aryl, hetaryl, aralkyl, hetarylalkyl, alkylaryl, alkylhetaryl and Y—$(CH_2)_m$—$NR^5$—$(CH_2)_q$ or together $(CH_2)_j$—X—$(CH_2)_m$ or $R^2$ and $R^4$ are together $(CH_2)_l$—X—$(CH_2)_m$, $R^5$, $R^{10}$ are hydrogen, $C_{1-4}$-alkyl, $C_{7-40}$-alkylphenyl, $R^6$, $R^7$, $R^8$, $R^9$ are hydrogen, methyl or ethyl, X is $CH_2$, $CHR^5$, oxygen, sulfur or $NR^5$, Y is $N(R^{10})_2$, hydroxyl, $C_{2-20}$-alkylaminoalkyl or $C_{3-20}$-dialkylaminoalkyl, n is an integer from 1 to 30 and j, k, l, m, q are an integer from 1 to 4 by reacting aldehydes or ketones of the formula II or III

(II)

with nitrogen compounds of the formula IV

(IV)

* * * * *